United States Patent
Park et al.

(10) Patent No.: US 11,325,874 B2
(45) Date of Patent: May 10, 2022

(54) METHOD FOR PREPARING A LINEAR ALPHA OLEFIN INCLUDING OXYGEN REMOVAL FROM THE FEED

(71) Applicants: SK Innovation Co., Ltd., Seoul (KR); SK Global Chemical Co., Ltd., Seoul (KR)

(72) Inventors: Chansaem Park, Daejeon (KR); Hyoseung Park, Daejeon (KR); Sungreal Son, Daejeon (KR); Inhyoup Song, Daejeon (KR); Woosung Jung, Daejeon (KR)

(73) Assignees: SK Innovation Co., Ltd., Seoul (KR); SK Global Chemical Co., Ltd., Seoul (KR)

( * ) Notice: Subject to any disclaimer, the term of this patent is extended or adjusted under 35 U.S.C. 154(b) by 0 days.

(21) Appl. No.: 17/263,194

(22) PCT Filed: Jun. 11, 2019

(86) PCT No.: PCT/KR2019/006976
§ 371 (c)(1),
(2) Date: Jan. 26, 2021

(87) PCT Pub. No.: WO2020/022642
PCT Pub. Date: Jan. 30, 2020

(65) Prior Publication Data
US 2021/0188736 A1    Jun. 24, 2021

(30) Foreign Application Priority Data
Jul. 26, 2018 (KR) .................. 10-2018-0087078

(51) Int. Cl.
C07C 2/30     (2006.01)
C07C 11/04    (2006.01)

(52) U.S. Cl.
CPC ............... *C07C 2/30* (2013.01); *C07C 11/04* (2013.01)

(58) Field of Classification Search
CPC .. C07C 7/12; C07C 11/04; C07C 7/13; C07C 2/30; C07C 2531/14; C07C 2523/26;
(Continued)

(56) References Cited

U.S. PATENT DOCUMENTS 5,786,431 A * 7/1998 Reagen ............... C07C 2/32
    526/113
6,124,517 A    9/2000 Kaminsky et al.
(Continued)

FOREIGN PATENT DOCUMENTS

JP    2007518679 A    7/2007
JP    2012523306 A    10/2012
(Continued)

OTHER PUBLICATIONS

Kim et al., "Ethylene oligomerizations to low-carbon linear alpha-olefins by structure modulated phenoxy-imine nickel(II) complexes combined with aluminum sesquichloride". Applied Catalysis A: General, 2005, vol. 287, pp. 98-107.

*Primary Examiner* — Ali Z Fadhel
(74) *Attorney, Agent, or Firm* — The Webb Law Firm

(57) ABSTRACT

Provided is a method for preparing a linear alpha olefin using a chromium-based catalyst, including the steps of: removing oxygen impurities by contacting an olefin with an oxygen adsorbent; injecting the olefin from which the oxygen impurities are removed; a chromium-based catalyst into a reactor; and oligomerizing the olefin in the reactor.

15 Claims, 1 Drawing Sheet

(58) Field of Classification Search
CPC ..... C07C 2531/24; C07C 2/36; C07C 5/2575; Y02P 20/52
See application file for complete search history.

(56) References Cited

U.S. PATENT DOCUMENTS

| | | | |
|---|---|---|---|
| 10,370,311 | B2 | 8/2019 | Peitz et al. |
| 10,508,065 | B2 | 12/2019 | Zilbershtein et al. |
| 2002/0003102 | A1* | 1/2002 | O'Rear ................. C10G 50/02 208/62 |
| 2004/0267071 | A1 | 12/2004 | Harris et al. |
| 2007/0185361 | A1* | 8/2007 | Buchanan ................ C07C 2/32 585/521 |
| 2009/0281365 | A1 | 11/2009 | Hatscher et al. |
| 2010/0228071 | A1 | 9/2010 | Kumar et al. |
| 2011/0027156 | A1* | 2/2011 | Eisinger .................... C07C 7/12 423/219 |
| 2012/0029258 | A1 | 2/2012 | Wohl et al. |
| 2015/0045603 | A1 | 2/2015 | Han et al. |
| 2017/0247298 | A1* | 8/2017 | Wagner ................... B01J 21/06 |

FOREIGN PATENT DOCUMENTS

| | | |
|---|---|---|
| KR | 1020090031893 A | 3/2009 |
| KR | 101017697 B1 | 2/2011 |
| KR | 1020130105126 A | 9/2013 |
| KR | 1020160140488 A | 12/2016 |
| KR | 1020170100579 A | 9/2017 |

* cited by examiner

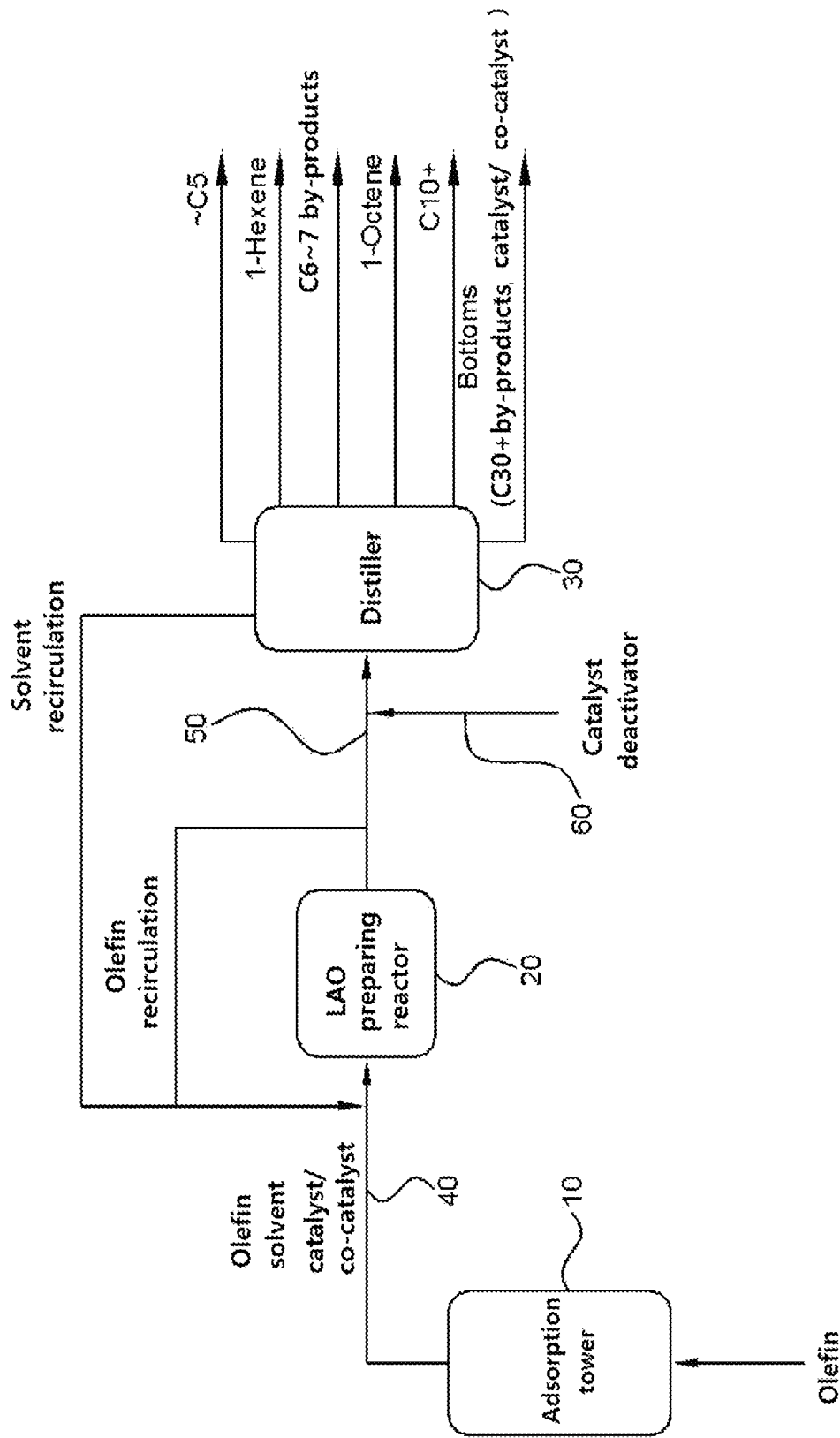

METHOD FOR PREPARING A LINEAR ALPHA OLEFIN INCLUDING OXYGEN REMOVAL FROM THE FEED

CROSS-REFERENCE TO RELATED APPLICATIONS

This application is the United States national phase of International Application No. PCT/KR2019/006976 filed Jun. 11, 2019, and claims priority to Korean Patent Application No. 10-2018-0087078 filed Jul. 26, 2018, the disclosures of which are hereby incorporated by reference in their entirety.

BACKGROUND OF THE INVENTION

Field of the Invention

The present invention relates to a method for preparing a linear alpha olefin, and more particularly, to a method for preparing a linear alpha olefin including an olefin purification process.

Description of Related Art

Ethylene is a raw material used as a basic raw material for the chemical industry, whose production and consumption amounts are judged as an indicator of the size of the nation's chemical industry. Typically, the ethylene has been used as a monomer for preparing a polymer such as polyethylene, and in some cases, a linear alpha olefin (LAO) having a carbon length (or chain) of about C4 to C40 has been prepared by adjusting a degree of polymerization and used to prepare various chemical substances.

Various catalysts such as a Ziegler-Natta catalyst and a chromium-based catalyst have been used as a catalyst for a process for preparing an LAO through oligomerization of the ethylene. Among them, impurities present in a feed ethylene may act as a catalyst poison in a process using a chromium-based catalyst to decrease a conversion rate of the ethylene, resulting in problems such as a decrease in reaction efficiency and a decrease in a yield of a C6 to C20 linear alpha olefin capable of added value increase.

As a specific example, oxygen ($O_2$) in the feed ethylene acts as the catalyst poison on the chromium-based catalyst, and may thus cause problems such as a decrease in the conversion rate in the process for preparing an LAO, a decrease in product purity, an increase in an operating cost for recycling unreacted ethylene, and an increase in a separation cost due to increased by-products.

Accordingly, there is a need for a technology capable of improving process efficiency by purifying the feed ethylene injected into the process for preparing an LAO and removing impurities.

SUMMARY OF THE INVENTION

An object of the present invention is to provide a method for preparing a linear alpha olefin capable of improving process efficiency in a process for preparing a linear alpha olefin, by solving problems such as a decrease in a conversion rate of olefin and a decrease in purity of a product occurring since impurities in a feed olefin act as a catalyst poison used in the process for preparing a linear alpha olefin to decrease catalytic activity.

Technical Solution

In one general aspect, there is a provided a method for preparing a linear alpha olefin, the method including the steps of: removing oxygen impurities by contacting an olefin with an oxygen adsorbent; injecting the olefin from which the oxygen impurities are removed, and a chromium-based catalyst into a reactor; and oligomerizing the olefin in the reactor.

The oxygen adsorbent may be CuO, NiO, $MoO_3$, zeolite 3A, activated alumina, or a mixture thereof.

The oxygen adsorbent may have a specific surface area of 100 to 900 $m^2/g$.

The step of removing the oxygen impurities may be performed by passing the olefin through an adsorption tower filled with the oxygen adsorbent.

The olefin may be injected into the adsorption tower at a gas hourly space velocity of 0.02 to 5 $hr^{-1}$.

The step of removing the oxygen impurities may be performed under a temperature of 10 to 100° C. and a pressure of 5 to 100 $kg/cm^2$.

The method for preparing a linear alpha olefin may further include, after the step of removing the oxygen impurities, a step of regenerating the oxygen adsorbent.

The oxygen adsorbent may be CuO, and the step of regenerating the oxygen adsorbent may be performed by passing a mixed gas of hydrogen and nitrogen through the adsorption tower at 100 to 200° C.

After the step of removing the oxygen impurities, an oxygen content in the olefin may be less than 100 ppm.

The chromium-based catalyst may be represented by $CrL^1(L^2)_p(X)_q$ or $Cr_2X^1{}_2L^1{}_2(L^2)_y(X)_z$ (where $L^1$ is a heteroligand, $L^2$ is an organic ligand, X and $X^1$ are each independently halogen, p is 0 or an integer of 1 or more, q is an integer of (oxidation number of Cr−p), y is an integer of 2 or more, and z is an integer of (2×oxidation number of Cr)−y).

The olefin may be ethylene.

Advantageous Effects

According to an aspect of the present invention, it is possible to solve problems such as a decrease in a conversion rate of olefin, a decrease in product purity, an increase in an operating cost for recycling unreacted ethylene, and an increase in a separation cost due to increased by-products, by reducing a content of impurities such as oxygen acting as a catalyst poison in a feed olefin, in the process for preparing a linear alpha olefin using a chromium-based catalyst.

Accordingly, the process efficiency in the process for preparing a linear alpha olefin may be improved.

BRIEF DESCRIPTION OF THE DRAWINGS

FIG. 1 is an exemplary schematic diagram of a process for preparing a linear alpha olefin according to an aspect of the present invention.

DESCRIPTION OF THE INVENTION

Unless otherwise defined, all terms (including technical and scientific terms) used herein have the general meaning understood by those skilled in the art to which the present invention pertains. Throughout the present specification, unless described to the contrary, "comprising" any component will be understood to imply the further inclusion of other elements rather than the exclusion of other elements. In addition, unless explicitly described to the contrary, a singular form includes a plural form in the present specification.

A feed olefin in a process for preparing a linear alpha olefin through oligomerization of olefin, may be contaminated with impurities such as oxygen, water, carbon monoxide, carbon dioxide, oxygenate, and sulfur during production and movement.

These impurities may act as a catalyst poison on the catalyst used in the process for preparing a linear alpha olefin to decrease a conversion rate of the reaction and a yield of a product, which may cause a decrease in process efficiency.

Specifically, in the process for preparing a liner alpha olefin using a chromium-based catalyst, oxygen impurities in the feed olefin may strongly act as the catalyst poison to generate problems such as a decrease in a conversion rate of ethylene and a decrease in a yield of a C6 to C20 linear alpha olefin capable of added-value increase, resulting in a decrease in quality of a product. Further, problems such as an increase in an operating cost for recycling unreacted olefins and an increase in a separation cost due to increased by-products may be caused, resulting in a decrease in overall process efficiency.

An aspect of the present invention for solving these problems provides a method for preparing a linear alpha olefin, the method including the steps of: removing oxygen impurities by contacting an olefin with an oxygen adsorbent; injecting the olefin from which the oxygen impurities are removed, and a chromium-based catalyst into a reactor; and oligomerizing the olefin in the reactor.

The method for preparing a linear alpha olefin according to an aspect of the present invention may include the step of removing oxygen impurities by contacting a feed olefin with an oxygen adsorbent, so that the problem such as a decrease in process efficiency occurring in the linear alpha olefin process using the above-described chromium-based catalyst can be solved.

The step of removing these oxygen impurities will be described in more detail.

In the method for producing a linear alpha olefin according to the present invention, the step of removing oxygen impurities by contacting the feed olefin with the oxygen adsorbent is not necessarily limited thereto, but may be performed by passing the olefin through an adsorption tower filled with the oxygen adsorbent.

The adsorption tower may use an adsorption tower configuration commonly used in the art, and the adsorption tower may be filled with an oxygen adsorbent and then passed through the feed olefin to adsorb and remove oxygen in the feed olefin.

Here, the oxygen adsorbent may be CuO, NiO, $MoO_3$, zeolite 3A, activated alumina, or a mixture thereof. Specifically, as confirmed in Examples to be described later, CuO may have the best oxygen removal ability under the same conditions.

Activated alumina is a superporous particle manufactured by the dehydroxylation of aluminum hydroxide, and examples of a commercially available product thereof include an A-201 by manufactured UOP, etc.

An aspect of a case of using two or more adsorbents may be performed in a form of dividing the adsorption tower into zones of two or more stages and filling the zones of the two or more stages with two or more types of adsorbents, respectively.

Specifically, for example, an aspect of a case of using two or more adsorbents may be formed in a form of dividing the adsorption tower into three stages, filling a lower stage with CuO, filling a middle stage with activated alumina, and filling an upper stage with zeolite 3A, but this is merely an example.

The oxygen adsorbent may have a BET specific surface area of 100 to 900 $m^2/g$, specifically 100 to 500 $m^2/g$, and more specifically 200 to 300 $m^2/g$, but the BET specific surface area is not limited thereto.

In addition, when two or more types of oxygen adsorbents are used, the BET specific surface area of each oxygen adsorbent may be independently determined within the above range.

In the method for preparing a linear alpha olefin according to an aspect of the present invention, the olefin may be injected into the adsorption tower at a gas hourly space velocity (GHSV) of 0.02 to 5 $hr^{-1}$. More specifically, the olefin may be injected into the adsorption tower at a GHSV of 0.07 to 2.5 $hr^{-1}$. Although the present invention is not necessarily limited thereto, oxygen in the ethylene may be removed at a concentration of less than 100 ppm within the above velocity range, which may be desirable. Here, the space velocity may be calculated by dividing an inflow flow rate ($m^3/h$) of the olefin by a reaction volume ($m^3$) in the reactor, and the reaction volume refers to a space in which the olefin may flow except for the space filled with the catalyst in the reactor.

In the method for preparing a linear alpha olefin according to an aspect of the present invention, the step of removing oxygen impurities may be performed under a temperature of 10 to 100° C. and a pressure of 5 to 100 $kg/cm^2$. However, the present invention is not necessarily limited thereto.

Meanwhile, the method for preparing a linear alpha olefin according to an aspect of the present invention may further include, after the step of removing the oxygen impurities, a step of regenerating the oxygen adsorbent.

The step of regenerating the oxygen adsorbent is additionally performed, thereby increasing a period of use of the adsorbent in the adsorption tower to minimize a process cost, which may be performed continuously by changing the state of each adsorbent tower to a cycle-type if the process is operated using one or more adsorbent tower, as described later.

The step of regenerating the adsorbent may be a step of cleaning the adsorbent by pushing out impurities such as oxygen adsorbed in the adsorbent with a cleaning gas, and removing the impurities and olefins remaining in the adsorption tower.

First, the regeneration method for each adsorbent will be described in more detail. In the case of a CuO adsorbent, the method may be performed by passing cleaning gas through the adsorption tower while maintaining the temperature of the adsorption tower at 100 to 200° C.

In this case, the cleaning gas may be a mixed gas of hydrogen ($H_2$) and nitrogen ($N_2$). In addition, a volume ratio of hydrogen and nitrogen in the mixed gas may be 5:95 to 95:5, but is not limited thereto.

Specifically, this cleaning process may be performed by heating the inside the adsorption tower to a temperature of 100 to 120° C. while injecting nitrogen, and then heating the inside the adsorption tower to a temperature of 150 to 200° C. while injecting a mixed gas containing hydrogen and nitrogen at a volume ratio of 5:95.

In the case of CuO, when the cleaning is performed by increasing the temperature to a range exceeding 200° C., there is a concern that the adsorption ability is lost due to deterioration. Thus, it may be preferable to perform a cleaning temperature as described above.

When zeolite 3A, NiO, MoO$_3$, or activated alumina is used as the adsorbent, the cleaning may be performed at 200 to 300° C. using nitrogen as the cleaning gas.

A specific process aspect of the step of removing the impurities in the method for preparing a linear alpha olefin according to an aspect of the present invention will be described below by taking a case of using two adsorption towers (a first adsorption tower and a second adsorption tower) filled with CuO as the adsorbent as an example.

First, the first adsorption tower performs an adsorption process, and the second adsorption tower performs a regeneration process while the adsorption process has been previously completed. Accordingly, the impurities in the olefin are adsorbed in the first adsorption tower, and the adsorbent is regenerated for the next adsorption process in the second adsorption tower. In this case, an outlet of the first adsorption tower may be in communication with the reactor of the process for preparing a linear alpha olefin through a valve, etc., and the outlet of the second adsorption tower may be controlled so as not to communicate through a valve, etc.

Once this step is completed, the process can be changed so that the first adsorption tower performs the regeneration process and the second adsorption tower performs the adsorption process, and these processes may be continuously circulated.

However, the present invention is not limited thereto, and it may be possible to use three or more adsorption towers and to circulate the above process by dividing the three or more adsorption tower into two groups.

In the step of removing the impurities in the method for preparing a linear alpha olefin according to an aspect of the present invention, an oxygen content in the olefin may be less than 100 ppm.

As confirmed in the examples to be described later, a C6 to C20 linear alpha olefin may be prepared in a high yield while achieving a high conversion rate, by making the oxygen content in the olefin to less than 100 ppm. In addition, it is possible to prevent a decrease in the life of the catalyst and to decrease a process cost by reducing the content of impurities acting as the catalyst position.

Hereinafter, the method for preparing a linear alpha olefin according to an aspect of the present invention will be described as a specific example with reference to FIG. 1.

A plant may include an adsorption tower 10 to remove impurities in an olefin, a reactor 20 in which oligomerization is performed, an injection line 40 for injecting a catalyst composition containing an olefin, a catalyst, a co-catalyst, and a solvent into the reactor 20, a discharge line 50 for discharging oligomerization reaction product from the reactor 20, a catalyst deactivator injection line 60 for injecting a catalyst deactivator into the discharge line 50, and a distiller 30 for separating the oligomerization reaction product.

First, the step of removing the impurities in the olefin described above is performed in the adsorption tower 10. Details of this step have been described above and thus will be omitted.

After the impurities are removed, the olefin from which the impurities such as oxygen were removed is injected into the linear alpha olefin preparation reactor 20 through the injection line 40 together with a chromium-based catalyst for oligomerization of the olefin, a co-catalyst, and a solvent.

The reactor 20 may include a batch reactor, a semi-batch reactor, and a continuous reactor, but is not limited thereto.

The chromium-based catalyst for the oligomerization reaction may be represented by $CrL^1(L^2)_p(X)_q$ or $Cr_2X^1{}_2L^1{}_2(L^2)_y(X)_z$ (where $L^1$ is a heteroligand, $L^2$ is an organic ligand, X and $X^1$ are each independently halogen, p is 0 or an integer of 1 or more, q is an integer of (oxidation number of Cr–p), y is an integer of 2 or more, and z is an integer of (2×oxidation number of Cr)–y). As the chromium-based catalyst, a catalyst having excellent reaction efficiency with an oligomer may be preferably used, but is not necessarily limited thereto.

The solvent may be an inert solvent. That is, any inert solvent that does not react with a chromium-based catalyst, a co-catalyst, and a catalyst deactivator may be used, and the inert solvent may include an aliphatic hydrocarbon. An aliphatic hydrocarbon is a saturated aliphatic hydrocarbon, including a linear saturated aliphatic hydrocarbon represented by $C_nH_{2n+2}$ (where n is an integer of 1 to 15), an alicyclic saturated aliphatic hydrocarbon represented by $C_mH_{2m}$ (where m is an integer of 3 to 8), and a saturated aliphatic hydrocarbon in which one or two or more lower alkyl groups having 1 to 3 carbon atoms are substituted. Specific examples of the saturated aliphatic hydrocarbon include one or more selected from the group consisting of hexane, heptane, octane, nonene, deccan, undecane, dodecane, tetradecane, 2,2-dimethylpentane, 2,3-dimethylpentane, 2,4-dimethylpentane, 3,3-dimethylpentane, 2,2,4-trimethylpentane, 2,3,4-trimethylpentane, 2-methylhexane, 3-methylhexane, 2,2-dimethylhexane, 2,4-dimethylhexane, 2,5-dimethylhexane, 3,4-dimethylhexane, 2-methylheptane, 4-methylheptane, cyclohexane, methylcyclohexane, ethylcyclohexane, isopropylcyclohexane, 1,4-dimethylcyclohexane, and 1,2,4-trimethylcyclohexane, but the saturated aliphatic hydrocarbon is not limited thereto.

The co-catalyst may be an organoaluminum compound, an organoaluminoxane, an organoboron compound, or a mixture thereof.

The organoaluminum compound may be a compound of $AlR_3$ (where each R is independently (C1-C12) alkyl, (C2-C10) alkenyl, (C2-C10) alkynyl, (C1-C12) alkoxy, or halogen) or $LiAlH_4$. However, the present invention is not limited thereto.

More specifically, the organoaluminum compound may be one or a mixture of two or more selected from the group consisting of trimethylaluminum (TMA), triethylaluminum (TEA), triisobutylaluminum (TIBA), tri-n-octylaluminum, methylaluminum dichloride, ethylaluminum dichloride, dimethylaluminum chloride, diethylaluminum chloride, aluminum isopropoxide, ethylaluminum sesquichloride, and methylaluminum sesquichloride. However, the present invention is not limited thereto.

The organoaluminoxane may be an oligomeric compound that may be prepared by adding water to trimethylaluminum, but the present invention is not limited thereto. The thus prepared aluminoxane oligomer compound may be linear, cyclic, cage, or a combination thereof.

Specifically, the organoaluminoxane may be selected from modified alkyl aluminoxane, for example modified methylaluminoxane (MMAO) as well as alkylaluminoxanes, for example, methylaluminoxane (MAO), ethylaluminoxane (EAO), tetraisobutylaluminoxane (TIBAO) and isobutylaluminoxane (IBRO). The modified methyl aluminoxane (manufactured by Akzo Nobel) may contain a hybrid alkyl group such as an isobutyl group or an n-octyl group in addition to a methyl group. However, the present invention is not limited thereto.

More specifically, the organoaluminoxane may be one or a mixture of two or more selected from the group consisting of methylaluminoxane (MAO), modified methylaluminoxane (MMAO), ethylaluminoxane (EAO), tetraisobutylaluminoxane (TIBAO), and isobutylaluminoxane (IBAO). However, the present invention is not limited thereto.

The organoboron compound is not limited thereto, but may be boroxine, NaBH4, triethyl borane, triphenyl borane, triphenylborane ammonia complex, tributylborate, triisopropylborate, tris(pentafluorophenyl)borane, trityl(tetrapentafluorophenyl)borate, dimethylphenyl ammonium(tetrapentafluorophenyl)borate, diethylphenylammonium (tetrapentafluorophenyl)borate, methyldiphenylammonium (tetrapentafluorophenyl)borate, or ethyldiphenylammonium (tetrapentafluorophenyl)borate, and may be used as the organoaluminum compound or a mixture with the organoaluminoxane.

In addition, in the oligomerization method of olefin according to an aspect of the present invention, a reaction temperature in the oligomerization reaction step may be performed at a temperature of 0 to 200° C., specifically at a temperature of 15 to 130° C., and more specifically at a temperature of 40 to 100° C., but is not limited thereto. A reaction pressure may be performed at a pressure of atmospheric pressure to 500 bar, specifically a pressure of atmospheric pressure to 100 bar, and more specifically a pressure of atmospheric pressure to 80 bar. However, the present invention is not limited thereto.

The reaction product discharged to the rear end of the reactor 20 may be transferred to the distiller 30 through the discharge line 50 and separated and recovered for each product through distillation.

Meanwhile, the catalyst deactivator that is injected into the discharge line 50 to suppress the occurrence of unnecessary side reactions may employ, without limitation, a catalyst deactivator used in the art.

Specifically, the catalyst deactivator may be 2-ethylhexanol.

On the other hand, for easy separation of C10 linear alpha olefin having a similar boiling point to 2-ethylhexanol, a material having a boiling point significantly higher or significantly lower than that of the C6 to C20 linear alpha olefin may be used.

As a specific example, an oxygen-containing inorganic material having a low boiling point may be $O_2$, $CO_2$, CO, $H_2O$, $NO_x$, $SO_x$, or a mixture thereof. Specifically, the oxygen-containing inorganic material having a low boiling point may be $O_2$, $CO_2$, CO, or a mixture thereof, and more specifically, $CO_2$ and $O_2$. More specifically, $CO_2$ may be obtained inexpensively as materials generated as by-products or exhaust gases in many industrial fields, and thus may be desirable in terms of improving process economy.

Here, $NO_x$ may be, for example, NO, $NO_2$, $N_2O$, $N_2O_3$, $N_2O_4$, $N_2O_5$, or a mixture thereof, but the present invention is not limited thereto.

Another specific example of the catalyst deactivator may include an organic compound having a high boiling point, including one or more of functional groups including at least one selected from the group consisting of oxygen, phosphorus, nitrogen, and sulfur, and having a number average molecular weight of 400 or more, and specifically, a phosphine-based compound having C31 or more, an amine-based compound having C31 or more, a thiol-based compound having C31 or more, or an alcohol-based compound having C31 or more. More specifically, the catalyst deactivator may be polypropylene glycol (PPG) represented by the following Formula 1:

[Formula 1]

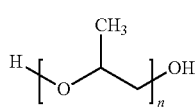

wherein n is 11 or more and 170 or less.

In Formula 1, n may be more specifically 12 or more and 150 or less, 17 or more and 130 or less, 17 or more and 110 or less, 17 or more and 35 or less, or 16 or more and 35 or less.

The distiller 30 is not limited to a specific type of distiller, and the number of stages of a distillation column may be adjusted, if necessary. The distillation method is also not limited to a specific distillation method, and an appropriate distillation method may be used, if necessary. For example, a plurality of distillation columns including a bottom reboiler (BTM reboiler) and an overhead condenser (OVHD condenser) and having the number of stages thereof of 50 or more and 100 or less, may be used.

Hereinafter, preferred examples and comparative examples of the present invention will be described. However, the following examples are only one of the preferred examples of the present invention, and the present invention is not limited thereto.

Examples 1 to 4 and Comparative Examples 1 to 3

Examples 1 and 2—Ethylene was injected into one adsorption tower filled with CuO particles (polymex-301, Sud-Chemie) having a BET specific surface area of 200 m$^2$/g at a gas hourly space velocity of 1.5 hr$^{-1}$ under a temperature of 50° C. and a pressure of 30 kg/cm$^2$ to remove impurities at a level of 0 ppm. Thereafter, the resultant product was injected into a batch reactor as follows to measure an amount of produced C6 to C20 linear alpha olefin and an amount of produced polymer with more carbon than the C6 to C20 linear alpha olefin, in the final product obtained by oligomerization.

The oligomerization catalyst prepared as follows was used: (bis-[(S,S)-(phenyl)$_2$PCH(methyl)CH(methyl)P(phenyl)$_2$ dichloride (μ-chloride) chromium] (5.3 μmol-Cr))

2.1 mg (5.3 umol) of tritetrahydrofuran chromium trichloride (CrCl$_3$(THF)$_3$) was dissolved in 1 mL of dichloromethane and a solution in which 2.4 mg (5.6 umol) of a (S,S)-(phenyl)$_2$PCH(methyl)CH(methyl)P(phenyl)$_2$ ligand compound was dissolved in 1 mL of dichloromethane was slowly added to the obtained solution to react for 60 minutes. Then, after stirring for another 5 minutes, 1.3 mg (5.6 umol) of sodium hexafluoroacetylacetonate was slowly added therein. Next, the reaction product was stirred for another 3 hours and then filtered using a 0.2 um syringe filter. Volatiles were removed from a filtrate under vacuum to obtain a dried dark green solid.

Thereafter, after washing a 2,000 mL stainless steel pressure reactor with nitrogen under vacuum, 1 L of methylcyclohexane (MCH), followed by modified methylaluminoxane (m-MAO3A, Akzo Nobel, 18 wt % in heptane) (1.57 g, 4 mmol) as a co-catalyst was injected, and the temperature of the reactor was raised to 60° C. Then, after 3.1 mg of bis-[(S,S)-(phenyl)$_2$PCH(methyl)CH(methyl)P(phenyl)$_2$ dichloride (p-chloride) chromium] (5.3 μmol-Cr) prepared above was injected, the pressure in the reactor was increased to 20 bar, and then the ethylene from which the impurities were removed was supplied while continuously maintaining the pressure to perform an oligomerization reaction while stirring at 250 rpm for 2 hours. Next, the stirring was stopped, all of the gaseous ethylene in the reactor was discharged, and the temperature of the reactor was cooled to 10° C.

Thereafter, a reaction solution was bubbled by injecting $CO_2$ gas, as the catalyst deactivator, using a dip tube at a pressure of 1 bar for 10 minutes to terminate the reaction, and then the reaction product was filtered and separated. Next, after drying 20 mL of the filtered product in a separate flask at 100° C. for 1 hour, GC-FID analysis was performed using heptane as an internal standard, and the amount of produced C6 to C20 linear alpha olefin and the amount of produced polymer with more carbon than the C6 to C20 linear alpha olefin were measured. These are summarized in Table 1. The amount of injected $CO_2$ is 5 times the total number of moles of aluminum in the co-catalyst based on the number of moles.

Examples 3 and 4—Examples 3 and 4 were performed in the same as that in Example 1, except that when the impurities were removed, a gas hourly space velocity of ethylene was adjusted to remove impurities to a level of <100 ppm of oxygen concentration in the ethylene after adsorption of the impurities.

Comparative Examples 1 to 3—Comparative Examples 1 to 3 were performed in the same as that in Example 1, except that no impurity adsorption step was performed.

TABLE 1

|  | $O_2$ concentration in ethylene (ppm) | Amount of produced C6-C20 linear alpha olefin (g) | Amount of produced polymer (g) |
| --- | --- | --- | --- |
| Example 1 | 0 | 426 | 0.09 |
| Example 2 | 0 | 407 | 0.07 |
| Example 3 | <100 | 423 | 0.57 |
| Example 4 | <100 | 450 | 0.83 |
| Comp. Example 1 | >1000 | 284 | 1.83 |
| Comp. Example 2 | >1000 | 157 | 1.63 |
| Comp. Example 3 | >1000 | 0 | 1.73 |

As can be seen from Table 1, in the case of examples from which oxygen impurities in ethylene were removed through adsorption, the amount of produced C6 to C20 linear alpha olefin was significantly higher than that of Comparative Examples in which no impurity adsorption was performed, and the amount of produced impurity polymer was very lower than that of Comparative Examples in which no impurity adsorption was performed.

[Examples 5 to 7 and Comparative Example 4]

Examples 5 to 7—The oligomerization reaction was performed in a continuous process while injecting ethylene, which had undergone impurity adsorption in the same manner as that in Example 1, into a continuous stirred tank reactor (CSTR) rather than a batch reactor. The oxygen concentration in the ethylene from which the impurities were removed was controlled by adjusting the gas hourly space velocity of ethylene injected into the adsorption tower.

Specifically, 1.0 g of an oligomerization catalyst (bis-[(S,S)-(phenyl)$_2$PCH(methyl)CH(methyl)P(phenyl)$_2$ dichloride (p-chloride) chromium] (5.3 μmol-Cr)) prepared in the same manner as that in Example 1 was dissolved in 12 L of methylcyclohexane and stored in a catalyst tank.

While methylcyclohexane was injected into the continuous stirred tank reactor (CSTR) at 2.0 L/hr, the reactor pressure was pressurized to 60 bar using a pressure control valve at the rear end of the reactor. After pressurization, the temperature inside the reactor was increased to 60° C. by increasing the temperature of a thermal fluid injected into a reactor jacket. After the completion of the temperature rise, modified methylaluminoxane (m-MA03A, Akzo Nobel, 18 wt % in heptane) (3.14 g/hr, 4 mmol) as a co-catalyst was continuously injected, and 6.2 mg/hr of bis-[(S,S)-(phenyl)$_2$PCH(methyl)CH(methyl)P(phenyl)$_2$ dichloride (p-chloride) chromium] (5.3 μmol-Cr)) stored in the tank was injected. Then, the reaction was initiated by continuously injecting the ethylene from which the impurities were removed at 0.6 kg/hr.

The reaction was terminated by continuously injecting 2-ethylhexanol as a catalyst deactivator at the rear end of the reactor, and the product was sampled. The sampled product was filtered, GC-FID analysis was performed, and the amount of produced C6 to C20 linear alpha olefin and the amount of produced polymer with more carbon than the C6 to C20 linear alpha olefin were calculated. These are summarized in Table 2.

Comparative Example 4—Comparative Example 4 was performed in the same as that in Example 5, except that the ethylene that has not undergone an impurity adsorption process was continuously injected.

TABLE 2

|  | $O_2$ concentration in ethylene (ppm) | Amount of produced C6-C20 linear alpha olefin (g/hr) |
| --- | --- | --- |
| Example 5 | 0 | 407.7 |
| Example 6 | 35.5 | 394.9 |
| Example 7 | 70.8 | 383 |
| Comp. Example 4 | 400 | 351.3 |

It can be confirmed from Table 2 that in the case of Examples in which oxygen impurities in ethylene were removed through adsorption, the amount of produced C6 to C20 linear alpha olefin was significantly higher than that of Comparative Examples in which no impurity adsorption was performed.

Examples 8 to 10

The linear alpha olefin was prepared in the same continuous process as that in Example 5, except that zeolite CaA, zeolite 5A, and zeolite 13X were used as the adsorbent, respectively, during the impurity adsorption.

TABLE 3

|  | $O_2$ concentration in ethylene (ppm) | Amount of produced C6-C20 linear alpha olefin (g/hr) |
| --- | --- | --- |
| Example 8 | 188 | 367.1 |
| Example 9 | 268 | 354 |
| Example 10 | 226 | 357.5 |

In Table 3, when zeolite CaA, zeolite 5A, and zeolite 13X were used, the amount of produced linear alpha olefin was higher than that in the case where no impurity adsorption was performed.

However, in comparison with Example 5 using CuO as the adsorbent, it was shown that the oxygen concentration in ethylene exceeded 100 ppm under the same conditions, and the amount of produced linear alpha olefin was relatively small.

DESCRIPTION OF REFERENCE NUMERALS

10: Adsorption tower 20: Reactor 30: Distiller 40: Injection line 50: Discharge line 60: Catalyst deactivator injection line

The invention claimed is:

1. A method for preparing a linear alpha olefin, the method comprising steps of:
removing oxygen impurities by contacting an olefin with an oxygen adsorbent;
injecting the olefin from which the oxygen impurities are removed, and a chromium-based catalyst into a reactor;
oligomerizing the olefin in the reactor; and
terminating the oligomerizing reaction by using a catalyst deactivator,
wherein the step of removing the oxygen impurities is performed under a temperature of 50 to 100° C.

2. The method of claim 1, wherein the oxygen adsorbent is CuO, NiO, $MoO_3$, zeolite 3A, activated alumina, or a mixture thereof.

3. The method of claim 1, wherein the oxygen adsorbent has a specific surface area of 100 to 900 $m^2/g$.

4. The method of claim 1, wherein the step of removing the oxygen impurities is performed by passing the olefin through an adsorption tower filled with the oxygen adsorbent.

5. The method of claim 4, wherein the olefin is injected into the adsorption tower at a gas hourly space velocity of 0.02 to 5 $hr^{-1}$.

6. The method of claim 4, further comprising, after the step of removing the oxygen impurities, a step of regenerating the oxygen adsorbent.

7. The method of claim 6, wherein the oxygen adsorbent is CuO, and the step of regenerating the oxygen adsorbent is performed by passing a mixed gas of hydrogen and nitrogen through the adsorption tower at 100 to 200° C.

8. The method of claim 7, wherein a volume ratio of hydrogen and nitrogen in the mixed gas is 5:95 to 95:5.

9. The method of claim 1, wherein the step of removing the oxygen impurities is performed under a pressure of 5 to 100 $kg/cm^2$.

10. The method of claim 1, wherein after the step of removing the oxygen impurities, an oxygen content in the olefin is less than 100 ppm.

11. The method of claim 10, wherein the oxygen content in the olefin is 0 ppm.

12. The method of claim 1, wherein the chromium-based catalyst is represented by $CrL^1(l^2)_p(X)_q$ or $Cr_2X^1_2L^1_2(L^2)_y(X)_z$ (where $L^1$ is a heteroligand, $L^2$ is an organic ligand, X and $X^1$ are each independently halogen, p is 0 or an integer of 1 or more, q is an integer of (oxidation number of Cr−p), y is an integer of 2 or more, and z is an integer of (2×oxidation number of Cr)−y).

13. The method of claim 1, wherein the olefin is ethylene.

14. The method of claim 1, wherein the catalyst deactivator is an oxygen-containing inorganic material selected from the group consisting of $O_2$, $CO_2$, CO, NO, $NO_2$, $N_2O$, $N_2O_3$, $N_2O_4$, $N_2O_5$ and a mixture thereof; an organic compound including one or more of functional groups including at least one selected from the group consisting of oxygen, phosphorus, nitrogen and sulfur, and having a number average molecular weight of 400 or more; or 2-ethylhexanol.

15. The method of claim 14, wherein the catalyst deactivator is an oxygen-containing inorganic material selected from the group consisting of $O_2$, $CO_2$, CO, NO, $NO_2$, $N_2O$, $N_2O_3$, $N_2O_4$, $N_2O_5$ and a mixture thereof; or an organic compound including one or more of functional groups including at least one selected from the group consisting of oxygen, phosphorus, nitrogen and sulfur, and having a number average molecular weight of 400 or more.

\* \* \* \* \*

UNITED STATES PATENT AND TRADEMARK OFFICE
CERTIFICATE OF CORRECTION

PATENT NO. : 11,325,874 B2
APPLICATION NO. : 17/263194
DATED : May 10, 2022
INVENTOR(S) : Park et al.

It is certified that error appears in the above-identified patent and that said Letters Patent is hereby corrected as shown below:

In the Claims

Column 12, Line 10, Claim 12, delete "$CrL^1(l^2)_P(X)_q$" and insert -- $CrL^1(L^2)_P(X)_q$ --

Signed and Sealed this
Twelfth Day of July, 2022

Katherine Kelly Vidal
*Director of the United States Patent and Trademark Office*